United States Patent [19]

Corby

[11] Patent Number: 4,983,634

[45] Date of Patent: Jan. 8, 1991

[54] TREATMENT OF MASTITIS AND APPLICATOR THEREFOR

[76] Inventor: Michael P. Corby, 19, Swinton Rise, Ravenshead, Nottinghamshire, England

[21] Appl. No.: 290,629

[22] Filed: Dec. 27, 1988

[30] Foreign Application Priority Data

Dec. 24, 1987 [GB] United Kingdom ................. 8730107

[51] Int. Cl.[5] ...................... A01N 37/18; A01N 25/02; A61K 31/165; A61M 1/06

[52] U.S. Cl. .................................... 514/622; 424/405; 604/74; 604/75

[58] Field of Search ........................ 514/622; 424/405; 604/74, 75

[56] References Cited

U.S. PATENT DOCUMENTS

| | | | |
|---|---|---|---|
| 3,950,554 | 4/1976 | Prince | 424/273 |
| 4,548,807 | 10/1985 | Westfall et al. | 424/45 |
| 4,637,814 | 1/1987 | Leiboff | 604/27 |

*Primary Examiner*—Merrell C. Cashion, Jr.

*Assistant Examiner*—Carlos Azpuru

*Attorney, Agent, or Firm*—Weintraub, DuRoss & Brady

[57] ABSTRACT

A method for treating mastitis which comprises the use of an infusion of an effective amount of (mon)oxychlorosene or sodium oxychlorosene in an aqueous carrier is disclosed.

A mastitis treatment infusion applicator which comprises a body portion including a compartment containing a first material which is an aqueous carrier, a cap portion including a compartment containing a second material which is (mon)oxychlorosene or sodium oxchlorosene, a seal arranged on either the body or cap portion to separate the two compartments, and seal-breaking means arranged on either the cap or body portion respectively, wherein the cap and body portion are movable relative to one another between a first position in which the seal is intact and a second position in which the seal is broken and in which the materials in the two compartments may come into contact. At least the surfaces contacting the second material being fluorinated is also disclosed.

8 Claims, 2 Drawing Sheets

TREATMENT OF MASTITIS AND APPLICATOR THEREFOR

FIELD OF THE INVENTION

This invention relates to the treatment of mastitis and to an applicator therefor; more particularly, it relates to the treatment of bovine mastitis, which may include so called "sub-clinical mastitis" and "summer mastitis", and to a mastitis treatment infusion applicator.

BACKGROUND OF THE INVENTION

Although in general terms the present veterinary method may be applied to all animals suffering from mastitis conditions, it will be largely illustrated with particular reference to dairy cattle. In short, mastitis is a condition caused by bacterial invasion of the milking organs resulting inter alia in painful inflammation and unwanted secretion. Numerous microorganisms are thought to contribute to the problem, but a handful of causative organisms are most common and hence serious, e.g. *Staph. coagulase positive, Str. dysgalactiae, uberis* and *agalactiae* and *E. coli.* "Summer mastitis" is commonly vectored by flies in non-lactating animals. In "sub-clinical" cases, animals suffer from the condition and may act as a source of infection, but do not manifest the full symptoms.

For many years, mastitis in dairy cattle has been treated by infusing comparatively small quantities of antibiotic suspensions into the udder after voiding as far as possible. Numerous such materials have been used and all involve several problems for the farmer/producer and the user/consumer.

As current antibiotics are long-acting after a course of treatment, the milking udder continues to excrete antibiotic-containing milk. The levels diminish with time, but remain problematic generally for between 6 and 10 milkings. During this period, the milk contains sufficient antibiotic active to inhibit significantly the growth of organisms in the milk, in particular those required for processing the milk into yoghurt or cheese, and also to have marked effects on the intestinal flora of consumers, particularly young children with high milk intake and low body weight. Also, it is generally recognized that a proportion of the population have allergic reactions to some antibiotics, particularly penicillins. For such reasons, in countries with legislation effectively controlling the sales of antibiotics, there are prescribed acceptable levels of antibiotic residues. Generally, the movement of such maxima is downwards and hence the period for which an animal's milk must be withheld from supply (i.e. discarded) is increasing. The use of prophylactic chlorine teat dips is also known.

It has now been found that (mon)oxychlorosene or sodium oxychlorosene in an aqueous medium is an effective treatment for mastitis in a lactating or non-lactating dairy animal. Such does not preclude other treatments and may indeed cooperate therewith. The active ingredient is known for use in human medicine as a disinfectant, but has never been suggested for veterinary use, specifically for the treatment of mastitis by infusion.

In general terms, the present invention relates to a method for treating mastitis which comprises the use of an infusion of an effective amount of (mon)oxychlorosene or sodium oxychlorosene in an aqueous carrier. Inter alia. the present invention provides the use of (mon)oxychlorosene or sodium oxychlorosene for the manufacture of a veterinary infusion medicament for treatment of mastitis. According to the present invention, the compositions used comprise the above active ingredient in an aqueous medium, which may be water or, preferably, saline solution. It is important that the infusion be prepared at the time of use.

According to Martindale, The Extra Pharmacopoeia, (mon)oxychlorosene is the hypochlorous acid complex of a mixture of the phenyl sulphonate derivatives of aliphatic hydrocarbons. It is a fine white powder, which dissolves slowly in water and then hydrolyses rapidly. It is currently commercially available under the trade name "Clorpactin".

Aqueous solutions of sodium (mon)oxychlorosene, in particular in physiological saline, prepared at the point of use, and infused into an infected cow's quarter udder have now been shown to be efficacious in treating mastitis. Generally, a course of 3 or 4 infusions is sufficient to alleviate the clinical symptoms of the condition. This is comparable with conventional antibiotic treatment.

The present active ingredient is thought to react in the infused quarter by releasing hypochlorous acid gas into the udder cavity and hence killing invading organisms. It is relatively short, but very strong acting. The active ingredient hence degrades during the reaction leaving a small amount of residue in the milk and subsequently extracted from the treated quarter(s), but such residue is non-inhibitory to all currently-recognized tests for inhibitory substances. In particular, it will not affect cheese and yoghurt starter cultures and is of proven low toxicity. For such reasons, it is possible to use the milk with only one milking needing to be discarded after a course of treatment.

Unlike treatment with antibiotics which may be systematically absorbed, the present method allows non-affected quarters to be milked normally during a course of treatment. Also, while some bacteria may prove antibiotic resistant, the same cannot be said in relation to the present active ingredient.

The present treatment utilizes dilute aqueous solutions of the active ingredient, for example up to 2.5% w/v. Commonly, a course of treatment would involve the use of, say, from 4 to 6 infusions of 40 ml aliquots of 1.25% w/v solutions. Normally, a course of treatment would coincide with the milking schedule over several days, but if desired the voiding/infusing might be repeated, say, hourly, so that an animal could be back "on-line" the next day, for example. Moreover, bearing in mind the problem of sub-clinical mastitis, periodic preventative treatments might be considered as minimal disruption would be involved.

Conventionally, an infusion of freshly-prepared material would be given using a syringe. However, the present invention also relates to a mastitis treatment infusion applicator which may advantageously be used for this purpose. For the present use, such an applicator is provided charged in separate compartments with the active ingredient and the vehicle, mixing being accomplished when required.

SUMMARY OF THE INVENTION

According to an aspect of the invention, a method for treating mastitis in all or part of a lactating or a non-lactating mammal's udder comprises:

(i) voiding said udder as far as possible;

(ii) preparing a fresh bactericidal solution of (mon)oxychlorosene or sodium oxychlorosene in a suitable carrier;

(iii) infusing said fresh solution through a teat into an infected area of said udder;

(iv) repeating steps (i) to (iii) as necessary until a full course of treatments is completed;

(v) said (mon)oxychlorosene or sodium oxychlorosene reacting in said treated udder portion to produce an antimicrobial compound and a non-toxic residue whereby usable milk is recoverable as soon as desired after completion of said treatments.

According to another aspect of the invention, a mastitis treatment infusion applicator is adapted to retain the chemical activity integrity of essential components of an infusion composition. The applicator comprises a body portion having a compartment containing a first material which is an aqueous carrier. A cap portion includes a compartment containing a second material which is (mon)oxychlorosene or sodium oxychlorosene. A seal is arranged on either the body or cap portion to separate the two components thereby preserving the essential activity of the (mon)oxychlorosene or sodium oxychlorosene. A seal breaking means is arranged on either the cap or body portion respectively, wherein the cap and body portion are movable relative to one another between a first position in which the seal is intact and a second position in which the seal is broken, and in which the materials in the two compartments may come into contact thereby providing a freshly prepared infusion composition immediately prior to infusion. At least the surfaces contacting the second material are fluorinated.

According to another aspect of the invention, the use of (mon)oxychlorosene or sodium oxychlorosene for the manufacture of an infusion composition for treatment of mastitis is provided.

According to another aspect of the invention, the use of a freshly prepared bactericidal solution of (mon)oxychlorosene or sodium oxychlorosene in an aqueous carrier for the treatment of mastitis is provided.

Various members are fluorinated, more particularly appropriate surfaces may be fluorinated after moulding.

Generally, the seal is arranged on the body portion and the seal breaking means is arranged on the cap portion. Preferably, the two portions can only move relative to one another when a tamper-proof strip, arranged between them, has been removed.

BRIEF DESCRIPTION OF THE DRAWINGS

Preferred embodiments of the invention are shown in the drawings wherein.

DETAILED DESCRIPTION OF THE DRAWINGS

Figure 1:
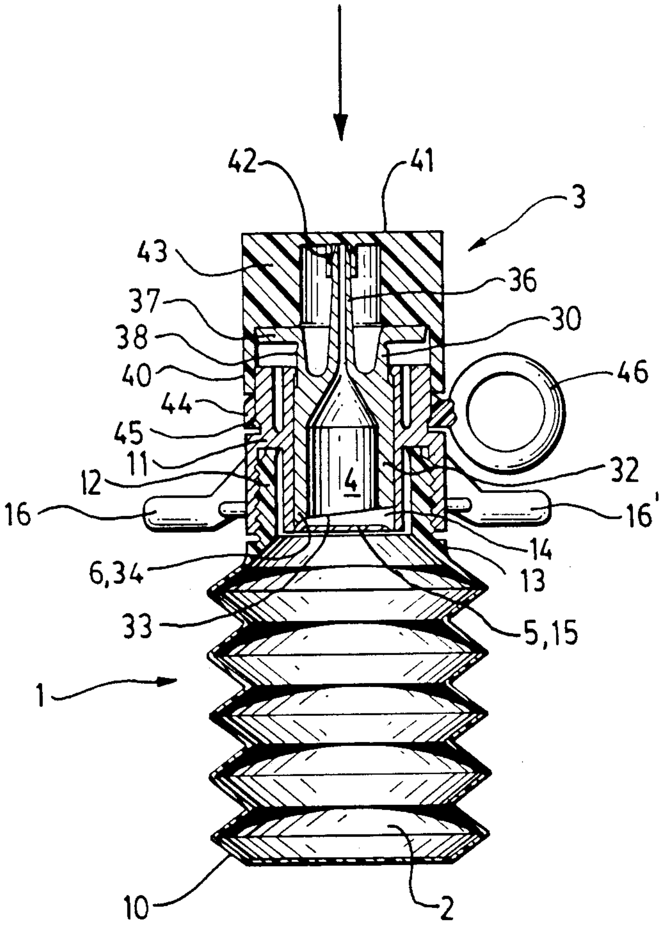
FIG. 1 is a sectional view of one preferred embodiment of the applicator of this invention.

Referring particularly to accompanying illustrative FIG. 1, the preferred applicator comprises a body portion 1 including a compartment 2 for a first material. This material is the vehicle, e.g. a saline solution.

Cap portion 3 includes a compartment 4 for a second material, which is the active ingredient, e.g. "Clorpactin".

A seal 5 is arranged on the body 1, between the two compartments 2, 4 and seal-breaking means 6 is arranged on the cap portion 3.

The cap 3 and body 1 are movable relative to one another between a first position (as illustrated) in which the seal is intact and a second position in which the seal is broken and the materials can mix. The direction of the movement is indicated by the arrow in the accompanying drawing.

The body 1 consists of a generally cylindrical container 10 holding the first material, and a head 11. The container 10 is preferably a compressible bottle. In the illustrated embodiment, head 11 is screwed tightly onto a threaded portion 12 on the neck 13 of the container 10; however, head 11 may be connected to the container 10 by means of a push-fit, a bayonet connection or ultrasonic welding.

Head 11 is generally tubular and includes a central cylindrical chamber 14. The seal 5 is molded as an integral part of the head 11, at the base of the chamber 14. Seal 5 comprises a disc 15 connected around its perimeter to the head 11 by a thin, breakable bridge. The head 11 includes a pair of oppositely radiating lugs 16, 16', the purpose of which will be explained later.

The cap 3 consists of a canula member 30 and a cover 40. The canula member 30 includes a hollow cylindrical portion 32 which fits in a sealed fashion into the chamber 14 of the head 11 of the container 1. The compartment 4 for the second material is within this cylindrical portion 32.

The base 33 of the portion 32 is truncated at an angle to the cylinder axis so that it presents a pointed section 34 for breaking the seal 5.

The compartment 4 leads to a canula 36 at the top of the canula member. At the base of the canula 36 there is a circular shoulder 37 beneath which there is a second annular recess 38.

When using "Clorpactin" those surfaces of the canula member 30 and the head 11 which would come into contact therewith are fluorinated.

The cover 40 clips onto the body portion 1 and presents a flat upper surface 41. A central seat 42 seals the canula 36 and internal ribs 43 engage the edge of the shoulder 37 of the canula member 30. At the base of the cover 40 there is a tear-off strip 44, having an internal lip 45 which clips into a corresponding recess on the head 11 to prevent the cover 40 from being inadvertently dislodged. The strip 44 also has a ring-pull 46.

When it is desired to use the applicator, the tear-off strip 44 is removed. This allows the cover 40 to be pressed towards the body 1. Ribs 43 in turn push the canula member 30 downwards so that the shoulder 37 comes to rest on the upper surface of the head 11 with the internal ribs of the head in recess 38. By this movement, the base 33 of the canula member 30 punches out the seal 5 and the materials are allowed to mix. Then the cover 40 is removed, the canula 36 is inserted in the teat and the resulting solution is injected into the udder.

The movement of the cover 40 towards the body 1 and the injection of the mixture are both achieved by holding the lugs 16, 16' with the fingers and either pressing the cap 40 or compressing the bottle 10 with the palm of the hand.

Figure 2A:
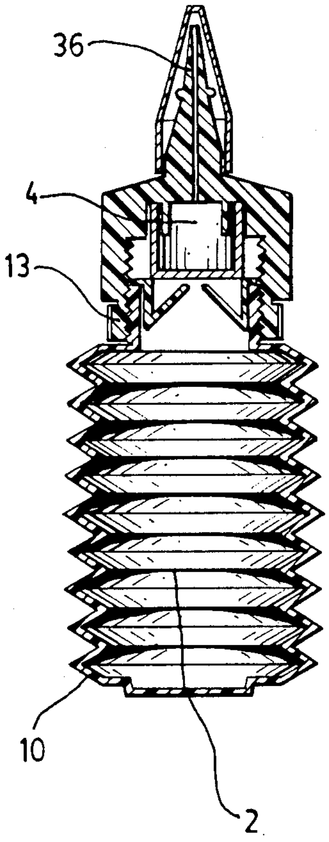
FIG. 2 is a combination section of an alternative preferred embodiment of this invention with the nozzle portion exploded to illustrate various components thereof.
Figure 2B:
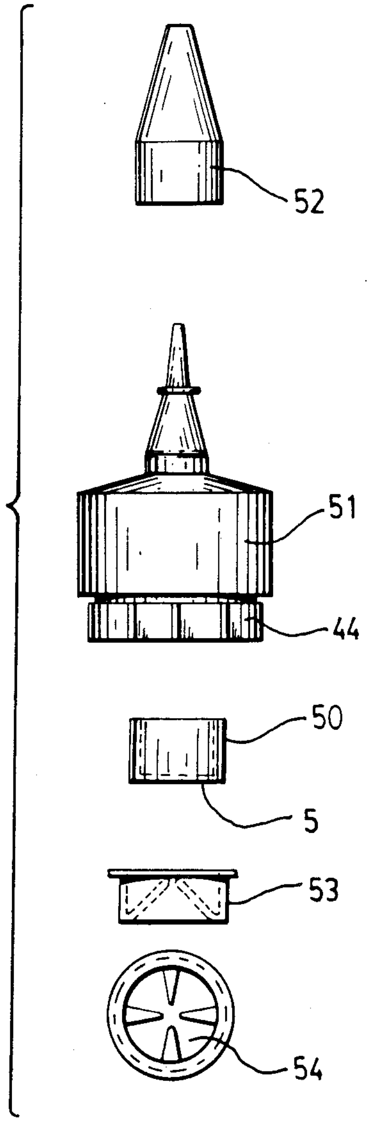

In the alternative embodiment of the present applicator illustrated in accompanying FIG. 2, the same numerals have been used for parts which correspond directly to parts of the preferred embodiment illustrated in accompanying FIG. 1.

In accompanying FIG. 2, the seal 5 is arranged on the cap portion 3 and the seal-breaking means is arranged on the body 1.

The seal 5 is at the base of a cup-shaped billet 50 which forms the compartment 4 for the second material. Around its rim, the billet 50 is fitted into an injector cap 51 which screws into the neck of container 10. Cap 51 has a tear-off strip 44, as in the preferred embodiment.

The canula portion 36 of the injector cap 51 is covered in an airtight manner by a nozzle cover 52.

Mounted in the neck 13 of the container 10 is the previously mentioned seal-breaking means. This takes the form of tubular member 53 at the base of which are four inwardly and upwardly extending spikes 54.

When the tear-off strip 44 is removed, the cap 51 can be further screwed onto the container 10. Such a movement forces the billet 50 to move downwards into the tubular member 53 where the spikes 54 pierce the seal 5, allowing the materials in the two compartments to mix.

The following illustrates the present invention:

The LD50 value of sterilized, γ-irradiated (2.5 megarads) "Clorpactin WCS-90" (sodium oxychlorosene) in a milk vehicle was found to be in excess of 5.00 g/kg by the oral route on rats.

In further safety studies, the tolerance of dairy cattle to the present treatment has been investigated:

Sixty one animals have been subjected to courses of six infusions at 2.5% w/v sodium oxychlorosene (double normal strength). No adverse effects were found. Studies have also been carried out on twelve infusions of 1.25% w/v sodium oxychlorosene at consecutive milkings (double normal length of course of treatment) and six infusions of 1.25% w/v sodium oxychlorosene using 80 mls (double normal volume). No adverse effects were found.

There is now reported a residue study using full normal courses of treatment (1.25% w/v sodium oxychlorosene).

The purpose of this investigation is to monitor the levels of residual "Clorpactin WCS-90" detectable in milk during a course of treatment.

The completed work, which takes the form of a series of individual studies, monitors the level of residues in milk from cows that were subjected to six infusions of a single normal strength "Clorpactin" dose (0.5 grams in 40 mls of physiological saline), both during infusion and for a series of milkings after the treatment was complete.

Analysis of the milk samples from each cow was by ion-pair reverse-phase chromatography. Calculation of the "Clorpactin" residues was, in the case of Study 01, by the peak height method, as the milk used for the standards was obtained from a different source from the cows under test (consequent detection limit 7 ppm). In studies, 02, 03 and 04 as the standards were made in milk obtained from the cow under test a few days prior to treatment, the peak area method was used (detection limit 1 ppm). Study 04, on mastitic cows was again by the peak area method with the standards being made up in milk obtained several days after treatment had finished.

Treatments:

Study 01

Two mid-lactation cows (Fresian) were selected for the trial, with each being subjected to one course of treatment with the "Clorpactin WCS-90". Treatments comprised six infusions, following six successive milkings, of "Clorpactin" at a single normal strength dose (0.5 gms per 40 mls of physiological saline)

Study 02

Two healthy mid-lactation cows (Fresian) were selected for this trial, with again each cow being subjected to a single course of treatment with "Clorpactin WCS-90". Study 02 differed from Study 01 in that a sample of the milk from the quarters under test was removed from the cow a few days prior to treatment, to enable accurate standards to be prepared.

Study 03

Three healthy mid-lactation cows (Fresian) were selected for the trial, with each being subjected to one course of treatment with the "Clorpactin WCS-90"to each of the four quarters of the animals.

The milk from all four quarters was monitored for residues during and after treatment, with the standards being made up in milk obtained from the quarters a few days before the trial.

Study 04

Two mastitic cows, used in the efficacy study, were monitored for residues in the milk from a point where the milk appeared to be normal. It was not possible to evaluate the severely mastitic milk as no standards may be prepared to evaluate milk that is constantly changing in composition. The standards used in this case were made in milk obtained some 4 days after the last sample was taken.

The results from these studies are detailed in the following Table and are largely self-explanatory. The first infusion occurred after milking 1, with the consequence that milking 1 represents the background. Means cited at the foot of the Table are calculated taking the $<7$ ppm and $<1$ ppm results as 7 and 1, respectively.

In the majority of cases, the background has been achieved by the 8th milking (one milking after treatment was completed).

| STUDY NUMBER | QUARTER STUDIED | ppm of Clorpactin detected in quarter milk — MILKING NUMBER 1 | 2 | 3 | 4 | 5 | 6 | 7 | 8 | 9 | 10 | 11 | LIMIT (ppm) | YIELD (Liters) |
|---|---|---|---|---|---|---|---|---|---|---|---|---|---|---|
| 01 | L.R. | <7 | 83 | 35 | 74 | 181 | 200 | 47 | <7 | <7 | <7 | <7 | 7 | 22 |
| | R.R. | <7 | <7 | 63 | 12 | 42 | 15 | 112 | <7 | <7 | <7 | <7 | 7 | 22 |
| 02 | L.R. | <1 | 38 | 255 | 42 | 71 | 48 | 40 | <7 | <7 | <7 | <7 | 1 | 25 |
| | L.F. | <1 | 113 | 255 | <1 | 184 | 195 | 202 | <1 | <1 | <1 | <1 | 1 | 20 |
| 03 | R.R. | <1 | 20 | 60 | 44 | 40 | 30 | 25 | 10 | <1 | NR | NR | 1 | 28 |
| | R.F. | <1 | 25 | 186 | 35 | 89 | 40 | 48 | <1 | <1 | NR | NR | 1 | " |
| | L.R. | <1 | 15 | 20 | 36 | 25 | 18 | 37 | 9 | <1 | NR | NR | 1 | " |
| | L.F. | <1 | 32 | 3 | 48 | 63 | 78 | 86 | 5 | <1 | NR | NR | 1 | " |
| 03 | R.R. | <1 | 10 | 8 | 15 | 46 | 14 | 11 | <1 | <1 | NR | NR | 1 | 23 |
| | R.F. | <1 | 10 | 86 | 70 | 42 | 47 | 58 | <1 | <1 | NR | NR | 1 | " |
| | L.R. | <1 | 25 | 54 | 33 | 82 | 54 | 51 | <1 | <1 | NR | NR | 1 | " |

-continued

| STUDY NUMBER | QUARTER STUDIED | ppm of Clorpactin detected in quarter milk — MILKING NUMBER 1 | 2 | 3 | 4 | 5 | 6 | 7 | 8 | 9 | 10 | 11 | LIMIT (ppm) | YIELD (Liters) |
|---|---|---|---|---|---|---|---|---|---|---|---|---|---|---|
| | L.F. | <1 | 34 | 26 | 42 | 60 | 25 | 92 | <1 | <1 | NR | NR | 1 | " |
| 03 | R.R. | <1 | 35 | 75 | 38 | 36 | 21 | 15 | <1 | <1 | NR | NR | 1 | 25 |
| | R.F. | <1 | 24 | 67 | 40 | 18 | 81 | 18 | <1 | <1 | NR | NR | 1 | " |
| | L.R. | <1 | 5 | 18 | 74 | 37 | 60 | 37 | <1 | <1 | NR | NR | 1 | " |
| | L.F. | <1 | 15 | 156 | 112 | 157 | 46 | 5 | <1 | <1 | NR | NR | 1 | " |
| 04 | — | NR | NR | NR | NR | NR | 21 | 25 | <1 | <1 | NR | NR | 1 | " |
| | — | NR | NR | NR | NR | 31 | 13 | 23 | <1 | NR | NR | NR | 1 | " |

MEAN OF ALL STUDIES IN HEALTHY COWS (01, 02, 03) 7 COWS, 16 QUARTERS
1.7 32 86 48 73 61 61 3.1 1.7
MEAN OF ALL QUARTERS INCLUDING MASTITIC COWS, MILKING NO. 8
(01, 02, 03, 04) 9 COWS, 18 QUARTERS
— — — — 2.8 —
KEY:
R.R. Right Rear
R.F. Right Front
L.R. Left Rear
L.F. Left Front First infusion carried out after milking number 1 on this Table.

The mean of results from samples taken after the one milking withdrawal period is 3.1 ppm.

10×3.1-31 ppm is far less than the minimum inhibitory concentration which is approximately 2000 ppm against *E. coli* and *St. faecalis* (intestinal flora).

A definition of nil effect level is greater than 2800 ppm. This is more than 600 times the mean level found. These calculations support a one milking withdrawal period. The conclusion from this series of experimental studies is that while the results obtained from the milk samples taken during treatment are variable, the levels of "Clorpactin" detected after treatment is complete quickly drops off to background. The data obtained, therefore, strongly supports a one milking withdrawal after treatment.

The inhibitory effect of "Clorpactin" on starter cultures was also investigated:

Raw whole milk was pasteurized and spiked with various concentrations of freshly prepared "Clorpactin". These samples were inoculated with the starters *Streptococcus thermophilus* and *Lactobacillus bulgarius* contained in natural yoghurt, incubated at 37° hours and the percent lactic acid determined by titratable acidity (BSI, 1741:1963).

Levels of up to 0.01% (100 ppm) "Clorpactin" had no effect on lactic acid production with starters in both the control and "Clorpactin"-spiked milks producing about 0.9% lactic acid. This is within the recommended level of 0 90–0.95% acidity. The mother culture of natural yoghurt had an acidity of 1.28% lactic acid which is rather high.

In conclusion, "Clorpactin" had no adverse affect on yoghurt starter culture activity, which is normally very sensitive to inhibitors.

An experimental study was conducted to determine if any absorption occurs between quarters during a course of treatment with "Clorpactin WCS-90".

The method used was to infuse two of the quarters of a healthy cow with a double normal strength course of treatment and to monitor each of the four quarters for "Clorpactin" residues, both during and after the trial. This with the assumption that if the material were being transferred between quarters by any mechanism it would be detected in the untreated quarters.

Analysis of the milk samples from each quarter was by ion-pair reverse-phase chromatography.

Calculation of the "Clorpactin" residues was by peak area with the milk used for the standards being prepared from milk obtained several days before treatment. Separate sets of standards were prepared for each quarter with the analysis being conducted "blind" i.e. the investigator was not informed beforehand which samples had been obtained from quarters which had been infused with "Clorpactin" during the course of treatments.

A single mid-lactation cow (Fresian) was selected for the trial. Two of the quarters were each infused with a double normal dose of "Clorpactin WCS-90" (2×0.5 g in 40 mls of physiological saline) on six consecutive occasions following 6 milkings.

The milk from all four quarters was monitored for residues both during and after the trial to determine if any transfer to untreated quarters had occurred.

The results from this study are presented in the following Table. The first infusion occurred after Milking No. 1, with the consequence that Milking 1 represents the background.

As may be seen, the level returns quickly to background after treatment is complete and is clear by Milking No. 8. No evidence of any "Clorpactin" was detected in the untreated quarters.

| MILKING NO | RESULT R.R. | R.F. | L.R. | L.F. |
|---|---|---|---|---|
| 1 | 0 | 0 | 0 | 0 |
| 2 | 112 | 43 | 0 | 0 |
| 3 | 128 | 10 | 0 | 0 |
| 4 | 264 | 160 | 0 | 0 |
| 5 | 154 | 445 | 0 | 0 |
| 6 | 33 | 138 | 0 | 0 |
| 7 | 92 | 226 | 0 | 0 |
| 8 | 10 | 36 | 0 | 0 |
| 9 | 0 | 0 | 0 | 0 |

Detection limit = 1 ppm of Clorpactin (0.1 ppm surfactant)
Results designated 0 ppm indicate <1 ppm, or no peak found.
KEY:
R.R. Right Rear
R.F. Right Front
L.R. Left Rear
L.F. Left Front The conclusion to be drawn is that, even with a double normal strength infusion, there is no mechanism of transference of "Clorpactin" to the untreated quarters, either during or after treatment.

The evidence of this study suggests that only milk from the treated quarter need be discarded, and that milk from the untreated quarters may at all times be added to the bulk tank supply.

In addition to the above safety aspects, the efficacy of the present treatment was also investigated.

Efficacy studies used half herds on a positive control and half herds on the experimental treatment. The protocol agreed was that herds were randomly split into two halves by number. Odd numbered cows received experimental treatment and even numbered cows received the positive control. Any animal sufficiently badly affected (i.e. systematically affected) should be the subject of a visit from a veterinary surgeon and was not included in the trial on either side.

Clinical symptoms were noted for each case at each milking and records were kept of each case. Milk samples of each infected quarter were sent to the MMB Laboratories for cell count and bacterial identification as follows:.

1. Initial (No treatment)
2. 24 hrs (before 2nd treatment)
3. 48 hrs (before 4th treatment)
4. 72 hrs (before 6th treatment)
5. 96 hrs (24 hrs post treatment)
6. 120 hrs (48 hrs post treatment)
7. 1 week (9 days post treatment)
8. 2 weeks (16 days post treatment)

A clinical cure is defined as the udder returning to normal function.

Experimental treatment:

40 ml of 1.25% w/v solution of sodium oxychlorosene infused 6 times at 6 milkings.

Positive control:

1 full tube of 100 mg procaine penicillin/100 mg dihydro-streptomycin sulphate infused 6 times at 6 milkings.

Five measurements can be made from the figures available:

(a) Clinical cure rate (b) Microbiological cure rate (c) Mean cell counts (d) Mean number of tubes to effect a clinical cure (e) Means number of tubes to effect a microbiological cure Clinical assay:

Experimental Routine

Odd numbered animals. Sodium oxychorosene. 40 ml 1.25% w/v. 6 times at successive milkings.

| Causative Organism | Total Cases of 6 Infusions | Clinical Cures | % Clinical Cures |
|---|---|---|---|
| *Staph. coagulase positive* | 72 | 65 | 90 |
| *E. coli* | 4 | 3 | |
| *Str. dysgalactiae* | 10 | 7 | 70 |
| *Str. uberis* | 25 | 19 | 76 |
| *Str. agalactiae* | 51 | 41 | 82 |

Positive Control

Even numbered animals.

Procaine penicillin/Dihydrostreptomycin sulphate. 6 times at 6 milkings.

| Causative Organism | Total Cases of 6 Infusions | Clinical Cures | % Clinical Cures |
|---|---|---|---|
| *Stanh. coagulase positive* | 38 | 26 | 68 |
| *E. coli* | 1 | 0 | |
| *Str. dysgalactiae* | 1 | 1 | |
| *Str. uberis* | 4 | 2 | |

-continued

| Causative Organism | Total Cases of 6 Infusions | Clinical Cures | % Clinical Cures |
|---|---|---|---|
| *Str. agalactiae* | 3 | 2 | |

Statistical treatment of the results shows that, at 95% confidence level, the present 1.25% w/v sodium oxychlorosene treatment is superior to the conventional antibiotic.

Somatic cell counts in milk from individual quarters is an indication of the state of health of that quarter. The higher the cell count, the greater is the degree of infection or the irritant effect in the udder.

The mean cell counts for all experimental milk samples submitted to the MMB are shown below. It is not always possible to obtain a cell count if the milk is obviously mastitic or if the sample deteriorates in transit. One problem with sodium oxychlorosene samples is that, due to lack of inhibitory effects, samples in transit may deteriorate quite rapidly. Samples containing antibiotic inhibitors are generally better protected from microbiological deterioration in transit. Some samples, when specifically needed for cell counts and not for causative organism assay, have been protected by the addition of formalin. This was carried out, for instance, when the irritancy studies were carried out.

Mean Cell Counts During and After Completed Treatments

| Day | Conventional antibiotic | n | Sodium oxychlorosene (1.25%) | n |
|---|---|---|---|---|
| 0 | 6326 | 27 | 6870 | 44 |
| 1 | 5570 | 24 | 6092 | 46 |
| 2 | 3092 | 23 | 4912 | 54 |
| 3 | 3919 | 21 | 4845 | 44 |
| 4 | 2307 | 18 | 3468 | 25 |
| 5 | 2637 | 14 | 2018 | 21 |
| 12 | 1372 | 22 | 1576 | 23 |
| 19 | 1358 | 20 | 965 | 21 |

Mean number of infusions to effect a clinical cure where a clinical cure is affected after up to 6 infusions.

| | |
|---|---|
| Experimental | |
| Mean number of infusions | n = 70 |
| Sodium oxychlorosene 1.25% w/v | x = 4.11 |
| | $\sigma n_1$ = 1.61 |
| Positive Control | |
| Mean number of infusions | n = 30 |
| Conventional antibiotic | x = 5.13 |
| | $\sigma n_1$ = 1.10 |

Analysis

Experimental vs Positive control. 72 degrees of freedom. $t=3.098$. Significant ($p<0.01$)

Although preferred embodiments of the invention have been described herein in detail, it will be understood by those skilled in the art that variations may be thereto without departing from the spirit of the invention or the scope of the appended claims.

I claim:

1. A method for treating mastitis in at least a portion of a mammal's udder comprising:

(i) substantially voiding said udder as far as possible;

(ii) preparing a fresh bactericidal solution comprising:

(a) a bactericide selected from the group consisting of (mon)oxychlorosene, sodium oxychlorosene and mixtures thereof and a suitable carrier;

(iii) infusing said fresh solution through a teat into an infected area of said udder;

(iv) repeating steps (i) to (iii) as necessary until a full course of treatment is completed; and wherein said bactericidal solution reacts in said treated udder portion to produce an antimicrobial compound and a non-toxic residue, and further wherein usable milk is recoverable one milking after completion of said treatments.

2. The method of claim 1 wherein said antimicrobial compound is hypochlorous acid gas.

3. A method of treating mastitis in at least a portion of mammal's udder having a teat thereon, comprising the steps of:

(i) substantially voiding said udder as far as possible;

(ii) breaking a seal in a treatment applicator to mix a bactericide stored in a first portion of said applicator with an aqueous carrier stored in a second portion of said applicator to prepare a fresh bactericidal solution, the bactericide selected from the group consisting of (mon)oxychlorosene, sodium oxychlorosene, and mixtures thereof;

(iii) inserting a tip of the applicator into the teat;

(iv) infusing a quantity of said fresh solution through the teat into an infected area of said udder; and (v) repeating steps (i) through (iv) as necessary until a full course of treatment is completed.

4. The method of claim 3 wherein said aqueous carrier is physiological saline.

5. The method of claim 4 wherein the concentration of said solution is no greater than 2.5% weight per volume.

6. The method of claim 5 wherein said concentration is 1.25% weight per volume.

7. The method of claim 6 wherein said volume is forty milliliters.

8. The method of claim 3, wherein the applicator comprises a compressible bottle, and wherein the infusion of the solution into the udder is accomplished by compressing the bottle.

* * * * *

UNITED STATES PATENT AND TRADEMARK OFFICE

CERTIFICATE OF CORRECTION

PATENT NO. : 4,983,634

DATED : January 8, 1991

INVENTOR(S) : Michael Peter Corby

It is certified that error appears in the above-identified patent and that said Letters Patent is hereby corrected as shown below:

On the title page, between items [76] and [21], insert the following:

--[73] Assignee: Diversey Corporation, Mississauga, Ontario, Canada; and United Guardian, Inc., Hauppauge, New York--

Signed and Sealed this

Thirtieth Day of June, 1992

*Attest:*

DOUGLAS B. COMER

*Attesting Officer*

*Acting Commissioner of Patents and Trademarks*